(12) United States Patent
Spielvogel et al.

(10) Patent No.: US 7,641,879 B2
(45) Date of Patent: Jan. 5, 2010

(54) METHODS OF SYNTHESIS OF ISOTOPICALLY ENRICHED BOROHYDRIDE AND METHODS OF SYNTHESIS OF ISOTOPICALLY ENRICHED BORANES

(75) Inventors: Bernard Spielvogel, Hubbards (CA); Kevin Cook, Hammonds Plains (CA)

(73) Assignee: SemEquip Inc., N. Billerica, MA (US)

( * ) Notice: Subject to any disclaimer, the term of this patent is extended or adjusted under 35 U.S.C. 154(b) by 492 days.

(21) Appl. No.: 11/047,165

(22) Filed: Jan. 28, 2005

(65) Prior Publication Data

US 2005/0169827 A1    Aug. 4, 2005

Related U.S. Application Data

(60) Provisional application No. 60/540,934, filed on Jan. 30, 2004.

(51) Int. Cl.
*C01B 6/15* (2006.01)
*C01B 6/17* (2006.01)
*C01B 6/19* (2006.01)
*C01B 6/21* (2006.01)
*C01B 6/23* (2006.01)
*C01B 35/18* (2006.01)

(52) U.S. Cl. ................. 423/288; 423/294
(58) Field of Classification Search ........... 423/288
See application file for complete search history.

(56) References Cited

U.S. PATENT DOCUMENTS

| 2,461,661 | A | * | 2/1949 | Schlesinger et al. ......... 423/288 |
| 2,642,453 | A | | 6/1953 | Lippincott |
| 2,939,762 | A | * | 6/1960 | Berner et. al. ............ 423/288 |
| 3,063,791 | A | | 11/1962 | Kollonitsch et al. |
| 4,115,520 | A | | 9/1978 | Dunks et al. |
| 4,115,521 | A | | 9/1978 | Dunks et al. |
| 4,153,672 | A | | 5/1979 | Dunks et al. |
| 4,209,510 | A | | 6/1980 | Spielvogel et al. |
| 4,709,083 | A | | 11/1987 | Spielvogel |
| 5,280,119 | A | | 1/1994 | Spielvogel et al. |
| 6,086,837 | A | | 7/2000 | Cowan et al. |
| 7,247,286 | B2 | * | 7/2007 | Ashby ....................... 423/288 |

FOREIGN PATENT DOCUMENTS

| WO | WO-94/06737 | | 3/1994 |
| WO | WO-03/044837 | A2 | 5/2003 |
| WO | WO-2004/003973 | A2 | 1/2004 |

OTHER PUBLICATIONS

Kawasaki et al. "Ultra-Shallow Junction Formation by $B_{18}H_{22}$ Ion Implantation" Presented at: Ion Implantation Technology 2004, Oct. 24-29, 2004, Taipe, Taiwan.
Adams et al. "A New Synthetic Route to Boron-10 Enriched Pentaborane(9) from Boric Acid and its Conversion to anti$^{10}B_{18}H^{22}$," *Journal American Chemical Society* 2002, 124, 7292-7293.
Jemmis et al. "Electronic Requirements for Macropolyhedral Boranes" *Chemical Reviews* 2002, 102, 93-144.
Jemmis et al. "A Unifying Electron-Counting Rule for Macropolyhedral Borane, Metallaboranes, and Metallocenes" *Journal of the American Chemical Society*, 2001, 123, 4313-4323.
Greenwood et al. *Chemistry of the Elements*, Chapter 6, Butterworth-Heinemann, Oxford, UK (1984).
Dunks et al. "Simplified Synthesis of $B_{10}H_{14}$ from $NaBH_4$ via the $B_{11}H_{14}^-$ Ion." *Inorganic Chemistry* 1981, 20, 1692-1697.
Dunks et al. "A One-Step Synthesis of $B_{11}H_{14}^-$ from $NaBH_4$." *Inorganic Chemistry* 1978, 17, 1514-1516.
Steinberg et al. "Preparation and Rate of Hydrolysis of Boric Acid Esters" *Industrial and Engineering Chemistry*, 1957, 49, 174-181.

* cited by examiner

*Primary Examiner*—Wayne Langel
(74) *Attorney, Agent, or Firm*—Edwards Angell Palmer & Dodge LLP; Peter F. Corless

(57) ABSTRACT

The invention provides new methods for the synthesis of isotopically enriched metal borohydrides, metal tetrahydroundecaborate salts, and decaborane from isotopically enriched $^{10}B$-boric acid or $^{11}B$-boric acid. The invention is particularly useful for synthesis of isotopically enriched sodium or lithium borohydride, $MB_{11}H_{14}$ (where M is Li, Na, K, or alkylammonium), and decaborane.

22 Claims, No Drawings

METHODS OF SYNTHESIS OF ISOTOPICALLY ENRICHED BOROHYDRIDE AND METHODS OF SYNTHESIS OF ISOTOPICALLY ENRICHED BORANES

CROSS-REFERENCE TO RELATED APPLICATION(S)

This application claims priority from U.S. Provisional Patent Application No. 60/540,934 which was filed on Jan. 30, 2004, which is incorporated by reference.

BACKGROUND

1. Field of the Invention

The invention provides new methods for synthesis of isotopically enriched borohydride compounds and methods of preparing isotopically enriched neutral or anionic boranes using isotopically enriched borohydride prepared by the methods of the invention as an intermediate. More particularly, the present invention provides improved methods of synthesis of isotopically enriched metal borohydrides from isotopically enriched boric acid and methods of synthesis of isotopically enriched neutral or anionic boranes having between 5 and 96 boron atoms, which methods comprise preparing an isotopically enriched metal borohydride as an intermediate in the preparation of the neutral or anionic borane.

2. Background

Large boron hydride compounds have become important feed stocks for boron doped P-type impurity regions in semiconductor manufacture. More particularly, high molecular weight boron hydride compounds, e.g., boron hydride compounds comprising at least a five (5) boron atom cluster, are preferred boron atom feed stocks for boron atom implantation.

An important aspect of modern semiconductor technology is the continuous development of smaller and faster devices. This process is called scaling. Scaling is driven by continuous advances in lithographic process methods, allowing the definition of smaller and smaller features in the semiconductor substrate which contains the integrated circuits. A generally accepted scaling theory has been developed to guide chip manufacturers in the appropriate resize of all aspects of the semiconductor device design at the same time, i.e., at each technology or scaling node. The greatest impact of scaling on ion implantation processes is the scaling of junction depths, which requires increasingly shallow junctions as the device dimensions are decreased. This requirement for increasingly shallow junctions as integrated circuit technology scales translates into the following requirement: ion implantation energies must be reduced with each scaling step. The extremely shallow junctions called for by modern, sub-0.13 micron devices are termed "Ultra-Shallow Junctions" or USJs.

Methods of manufacturing boron doped P-type junctions have been hampered by difficulty in the ion-implantation process using boron. The boron atom, being light (MW=10.8), can penetrate more deeply into a silicon substrate and diffuse throughout the substrate lattice rapidly during annealing or other elevated temperature processes.

Boron clusters or cages, e.g., boranes have been investigated as a feed stock for delivering boron to a semiconductor substrate with reduced penetration. For example, boron ions may be implanted into a substrate by ionizing boron hydride molecules of the formula $B_nH_m$ (where 100>n>5 and m≦n+8) and an ion source for use in said implantation methods.

Certain preferred compounds for use in the boron ion implantation methods included decaborane ($B_{10}H_{14}$) and octadecaborane ($B_{18}H_{22}$).

Large boron hydride compounds, that is boron compounds having between 5 and about 100 (more typically between 10 and about 100 or between 5 and about 25 boron atoms) are preferred for use in molecular ion implantation methods for delivering boron atoms to a semiconductor substrate. Typically two or more structural isomers exist of large boron hydride compounds, e.g., two or more compounds having the same chemical formula but different structural arrangement of boron atoms in the cage structure. In addition, two or more structurally related boron hydride compounds having the same number of boron atoms but different numbers of hydrogen atoms have been isolated for various sized boron clusters. Such compounds are frequently referred to as closo ($B_nH_n$), nido($B_nH_{n+2}$), arachno ($B_nH^{n+4}$), hypho ($B_nH_{n+6}$), conjuncto ($B_nH_{n+8}$), and the like. Thus, a plurality of different boron hydride species, including structural isomers and compounds containing various amounts of hydrogen are frequently known for boron hydrides having n boron atoms. See, for example, Jemmis, et al., *J. Am. Chem. Soc.*, v. 123, 4313-4323 (2001), which provides a review of various macropolyhedral boranes and known compounds having n boron atoms and various amounts of hydrogen.

International patent application WO 03/044837, (Applied Materials, Inc, Santa Clara Calif.) recites methods of ion implantation in which an isotopically enriched boron compounds including $^{11}B$ enriched compounds are ionized and then implanted into a substrate. The '837 publication recites the preparation of the iosotopically enriched boranes by the method recited in U.S. Pat. No. 6,086,837 (Cowan, et al.), which methods are reported to be the current industrial process for the preparation of boranes isotopically enriched in $^{10}B$ or $^{11}B$.

Cowan (U.S. Pat. No. 6,086,837) recites a method of preparing B-10 enriched decaborane starting with B-10 enriched boric acid. The Cowan preparation of either B-10 or B-11 enriched boron hydrides begins with boric acid and involves a multitude of synthetic and purification steps. More particularly, the Cowan process for conversion of boric acid into an alkali metal borohydride involves numerous time consuming steps and results in a relatively low yield of valuable B-10 enriched borohydride which must then be subjected to further reactions to obtain final product.

Thus, the Cowan method starts with the preparation of B-10 methylborate from boric acid and methanol using an azeotropic distillation method. The methylborate is separated from remaining methanol by freeze recrystallization by means of three one step procedures to produce an 80% yield of trimethylborate. The trimethylborate is then added to a suspension of sodium hydride in mineral oil at 220° C.-250° C. and heated for 12 hrs. For safety, a metal reflux condenser is required. Isolation of the formed borohydride requires special attention. First, the excess sodium hydride is destroyed by pouring the mineral oil mixture into a mixture of ice and water, a rather exothermic process evolving gaseous hydrogen. Then the aqueous borohydride is separated from the mineral oil by decantation or use of separatory funnel. The aqueous borohydride must be purged of methanol by either heating to 60° C. and purged with a nitrogen stream or by removal under reduced pressure. The resulting aqueous solution is comprised of sodium hydroxide and the B-10 enriched borohydride. Carbon dioxide gas is bubbled through the solution converting the sodium hydroxide to sodium carbonate. The resulting slurry is then extracted with n-propylamine and the n-propylamine evaporated to yield final product. The solubilty of sodium borohydride in n-propylamine is limited and appreciable volumes of the volatile solvent are needed. Typical yields of 45-65% are obtained. A total of ten time consuming steps are required to prepare isotopically enriched sodium borohydride by the procedure recited in Cowan.

U.S. Pat. No. 2,642,453, issued to Lippincott, relates to methods of preparing borates of tertiary alcohols such as methods of preparing tri(tert-butyl)borate and the like by condensation of boric acid and a tertiary alcohol and water removal by fractional distillation of an azeotrope. The preparation and rate of hydrolysis of a variety of boric acid esters was recited by H. Steinberg and D. L. Hunter in *Industry and Engineering Chemistry*, v. 49, No. 2, (1957) p. 174-181.

U.S. Pat. No. 3,063,791, issued to Kollonitsch, et al., relates to method of preparing natural abundance alkali and alkaline earth metal borohydrides from boric acid by contacting an intermediate trialkylborate with alkali metal aluminum hydride. Kollonitsch does not provide methods of synthesis of isotopically enriched borohydrides.

Dunks and coworkers recite methods of preparing $MB_{11}H_{14}$ salts and decaborane ($B_{10}H_{14}$) from metal borohydride or $MB_3H_8$ starting materials. U.S. Pat. Nos. 4,115,520, 4,115,521, and 4,153,672, each of which was issued to Dunks, et al., relate to methods of synthesis of decaborane and methods of synthesis of $B_{11}H_{14}^-$.

Although there have been reports in the literature for the synthesis of isotopically enriched boron, these synthetic routes are lengthy and often produce compounds in notably low yields. It thus would be desirable to have new methods to synthesize isotopically enriched borohydride and isotopically enriched boranes from isotopically enriched boric acid. It would be particularly desirable to have new methods to synthesize isotopically enriched $MBH_4$, $MB_{11}H_{14}$, $B_{10}H_{14}$ and methods of preparing isotopically enriched large boranes of the formula, $B_nH_m$, (where n is between 12 and 96 and $m \leq n+8$).

SUMMARY OF THE INVENTION

We have now found new methods for the preparation of isotopically enriched metal borohydride, isotopically enriched decaborane, and isotopically enriched metal tetradecahydroundecaborate salt ($MB_{11}H_{14}$). Moreover, the methods of synthesis for metal tetradecahydroundecaborate salt and decaborane incorporate the instant methods of preparing isotopically enriched metal borohydride. The invention is particularly useful for synthesis of isotopically enriched $MBH_4$, $MB_{11}H_{14}$ and $B_{10}H_{14}$, where M is a monovalent or divalent cation.

In one aspect, the invention provides an improved method of synthesizing an isotopically enriched metal boron hydride, the method comprising the steps of:
(a) providing isotopically enriched boric acid;
(b) contacting the isotopically enriched boric acid with an alcohol under conditions conducive to formation of an isotopically enriched borate; and
(c) reducing the isotopically enriched borate with a metal aluminum hydride under conditions conducive to formation of isotopically enriched metal borohydride.

In another aspect, the invention provides an improved method of preparing isotopically enriched metal tetradecahydroundecaborate salt, the method comprising the steps of:
(a) providing isotopically enriched metal borohydride prepared by any of the methods provided herein; and
(b) contacting a solution of the isotopically enriched metal borohydride with a compound of the formula, R—X or isotopically enriched $BY_3$(ligand), under conditions conducive to the formation of a metal tetradecahydroundecaborate salt, wherein
R is alkyl, alkenyl, or aralkyl;
X is fluoro, chloro, bromo, iodo, alkylsulfonate, or arylsulfonate;
Y is fluoro, chloro, or bromo; and
ligand is absent, an ether, an amine, or a pyridine.

In yet another aspect, the invention provides methods of preparing isotopically enriched decaborane, the method comprising the steps of:
(a) providing isotopically enriched metal tetradecahydroundecaborate salt according the to methods provided herein; and
(b) contacting the isotopically enriched metal tetradecahydroundecaborate salt with an oxidizing agent having an electrode potential of at least about 0.6 volts at a temperature of between about –10° C. and about 50° C. under conditions conducive to oxidation of the metal tetradecahydroundecaborate salt.

The methods of the invention provide high yields of isotopically enriched metal borohydrides, isotopically enriched metal tetradecahydroundecaborate salts and isotopically enriched decaborane with fewer synthetic and purification steps compared to methods recited in the literature. Moreover, the methods of synthesis are suitable for preparing isotopically enriched decaborane and isotopically enriched metal tetradecahydroundecaborate salts which are suitable for use as starting materials for a variety of larger isotopically enriched boranes, or mixture of isotopically enriched boranes, in which each borane contains n boron atoms (12<n<100) wherein the methods comprise preparing at least one isotopically enriched $MBH_4$, isotopically enriched $MB_{11}H_{14}$ and/or isotopically enriched $B_{10}H_{14}$ by the methods of the invention. Preferred methods of synthesis generate product mixtures having substantially uniform chemical composition, e.g., preferred methods of synthesis provide a compound of the formula $B_nH_m$, which may be present as one or more structural isomers. In certain other aspects, methods of synthesis which provide a mixture of boranes, each of which comprises n boron atoms and a different number of hydrogen atoms, are also contemplated by the present invention, in part because, such mixtures of various n boron atom boranes will generate substantially the same mixture of molecular ions when subjected to ionization during an implantation process as a borane composition comprising a single borane of the formula $B_nH_m$. Thus, methods which provide two or more borane compounds such as $B_nH_m$, $B_nH_p$, and the like, where m≠p and the absolute difference between m and p is less than about 8, are also contemplated by the invention.

Other aspects of the invention are discussed infra.

DETAILED DESCRIPTION OF THE INVENTION

Remarkably, we have discovered new methods for the preparation of boron hydride and salts thereof, including metal borohydrides, decaborane, metal tetradecahydroundecaborate salts, and boron hydride compounds prepared from same. The methods of the invention provide an efficient synthetic procedure for the preparation of isotopically enriched boranes and boron containing compounds.

In one preferred aspect, the invention provides a method of synthesizing an isotopically enriched metal borohydride, the method comprising the steps of:

(a) providing isotopically enriched boric acid;
(b) contacting the isotopically enriched boric acid with an alcohol under conditions conducive to formation of an isotopically enriched borate; and
(c) reducing the isotopically enriched borate with a metal aluminum hydride under conditions conducive to formation of isotopically enriched metal borohydride.

In certain preferred methods of metal borohydride synthesis provided by the invention, the isotopically enriched borate prepared by esterification of boric acid is a compound of Formula I:

[(RO)$_2$B—O—]$_n$—R'  I wherein
each occurrence of R is independently selected from the group consisting of linear or branched alkyl, cycloalkyl, cycloalkyl-alkyl, alkenyl, aryl, aralkyl, haloalkyl, and alkylether, or
two R groups taken in combination form a α,ω-alkylene group or a 1,2-cylcoalkylene group each of which may be optionally substituted with one or more groups selected from the group consisting of alkyl, alkenyl, cycloalkyl, cycloalkyl-alkyl, aryl, aralkyl, and alkoxy;
n is 1 or 2; and
R' is selected from the group consisting of alkyl, alkenyl, aryl, aralkyl, haloalkyl, and alkylether when n=1, or R' is a α,ω-alkylene group or a 1,2-cylcoalkylene group each of which may be optionally substituted with one or more groups selected from the group consisting of alkyl, alkenyl, cycloalkyl, cycloalkyl-alkyl, aryl, aralkyl, and alkoxy when n=2.

In certain preferred methods of isotopically enriched metal borohydride synthesis provided by the invention include those methods in which the isotopically enriched borate is a compound of the formula, B(OR)$_3$, wherein R is independently selected at each occurrence from the group consisting of linear or branched C$_{1-10}$alkyl, phenyl, benzyl, C$_{3-8}$cycloalkyl, C$_{3-8}$cycloalkyl-C$_{1-10}$alkyl, C$_{2-10}$alkenyl, C$_{1-10}$alkoxy, C$_{1-10}$haloalkyl, and C$_{2-10}$alkylether.

In other preferred methods of isotopically enriched metal borohydride synthesis provided by the invention include those methods in which the isotopically enriched borate is a compound of the formula, B(OR)$_3$, wherein each occurrence of R is the same and R is selected from the group consisting of linear or branched C$_{1-10}$alkyl, phenyl, benzyl, C$_{3-8}$cycloalkyl, C$_{3-8}$cycloalkyl-C$_{1-10}$-alkyl, C$_{2-10}$alkenyl, C$_{1-10}$alkoxy, C$_{1-10}$haloalkyl, and C$_{2-10}$alkylether.

In certain other preferred methods of synthesis of isotopically enriched metal borohydrides provided by the invention, the isotopically enriched borate is a compound of Formula II:

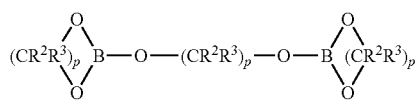

II wherein R$^2$ and R$^3$ are independently selected at each occurrence from the group consisting of hydrogen, linear or branched alkyl, cycloalkyl, cycloalkyl-alkyl, alkenyl, aryl, aralkyl, haloalkyl, and alkylether; and
p is an integer selected from 1-5.

Certain preferred isotopically enriched borates of Formula II, which are suitable for use in the methods of synthesis of isotopically enriched metal borohydrides, include isotopically enriched borates of Formula III:

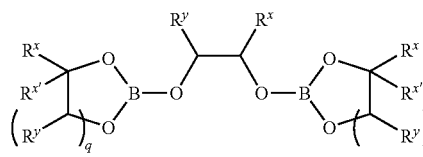

III wherein R$^x$, R$^{x'}$, and R$^y$ are independently selected at each occurrence from the group consisting of hydrogen, linear and branched C$_{1-10}$alkyl, C$_{1-10}$alkoxy, and C$_{3-8}$cycloalkyl, or R$^x$ and R$^y$, taken in combination form a α,ω-alkylene group; and q is 1 or 2. Certain particularly preferred compounds of Formula III include those in which R$^x$, R$^{x'}$, and R$^y$ are selected from the group consisting of hydrogen or linear or branched C$_{1-4}$alkyl. Particularly preferred compounds of Formula III include those in which R$^x$, R$^{x'}$, and R$^y$ are methyl and q is 1 or 2. The compound prepared by condensation of boric acid and 2-methyl-2,4-pentanediol, e.g., tris(2-methyl-2,4-pentandiolate)diborate, is a particularly preferred compound of Formula III.

Although the stoichiometry of the alcohol and isotopically enriched boric acid of the esterification step is not particularly limited, it is generally preferred to have a sufficient quantity of alcohol to effect complete conversion of the boric acid to borate. More preferably, the isotopically enriched boric acid is contacted with at least three equivalents of the alcohol.

In certain particularly preferred esterification steps, the isotopically enriched boric acid is contacted with at least three equivalents of a linear or branched C$_{1-10}$alkanol or at least one and a half (1.5) equivalents of a C$_{2-10}$alkanediol. More preferably, the isotopically enriched boric acid is contacted with between about three and six equivalents of a linear or branched C$_{1-10}$alkanol or between about one and a half (1.5) to three equivalents of a C$_{2-10}$alkanediol. In certain particularly preferred esterification steps, the isotopically enriched boric acid is contacted with about three equivalents of a linear C$_{2-10}$alkanol or about one and a half (1.5) equivalents of a linear or branched 1,2-C$_{2-10}$alkanediol.

Preferred esterification steps comprise contacting the isotopically enriched boric acid with the alcohol under dehydrative conditions, e.g., under conditions conducive to the consumption or elimination of water from the reaction mixture. Although any means of water removal is acceptable, and may include as non-limiting examples, molecular sieves, silicates, anhydrous salts such as calcium chloride, magnesium sulfate, sodium sulfate, and the like, or fractional distillation of water or an azeotrope thereof. In general, fractional distillation of water or a water:solvent azeotrope are generally preferred means of removing water from the esterification reaction mixture. Preferred methods of water removal from the esterification reaction mixture include fractional distillation of an azeotrope of water and at least one solvent selected from toluene, xylene, mesitylene, benzene, 1,2-dichloroethane, and mixtures thereof.

The esterification step is typically conducted at an elevated temperature, e.g., a temperature of at least about 25° C. More preferably, the esterification is conducted at a temperature of more than about 30° C., 40° C., 50° C., 60° C., 70° C., or more than about 80° C. In certain particularly preferred embodiments, the esterification step is conducted at a temperature of between about 90° C. and about 200° C., between about 95° C. and about 175° C., or at a temperature sufficient to reflux the reaction mixture.

In certain aspects of the invention, methods of isotopically enriched borohydride synthesis comprise a borate reduction step which comprises contacting the isotopically enriched borate (e.g., $B(OR)_3$) with a mixture of a metal aluminum hydride and a solvent. Typically preferred metal aluminum hydrides comprise at least one and more preferably two, three, or four hydride ligands bound to an aluminum atom. Preferred metal aluminum hydrides include those compounds in which the metal is a group I or group II metal such as lithium, sodium, potassium, calcium, magnesium or the like. Particularly preferred metal aluminum hydrides include lithium aluminum hydride (LAH), sodium aluminum hydride, and mixture thereof.

The methods provided by the instant invention are suitable for the preparation of metal borohydrides and metal borodeuterides. Thus, substitution of a metal aluminum deuteride having at least one or more preferably two, three or four deuteride ligands bound to an aluminum atom may be used in the methods of the invention in place of the metal aluminum hydrides to prepare isotopically enriched metal borodeuterides.

In preferred methods of the invention, the isotopically enriched borate is added to a mixture of at least one metal aluminum hydride and at least one organic fluid (e.g., organic solvent). Preferred solvents which are suitable for use in the reduction step include, but are not limited to, oxiranes, ethers, polyethers, and mixtures thereof. More preferred solvents are typically selected from 5 to 7 membered heterocycles having 1 or 2 oxygen ring atoms, $(C_{1-10}alkyl)_2$ethers, $Me(OCH_2CH_2)_nOMe$ (where n is 1 to about 5), and mixtures thereof More preferably the solvent is selected from diethyl ether, tetrahydrofuran, 1,3-dioxolane, 1,4-dioxane, 1,3-dioxane, methyl-tert-butyl ether, dimethoxyethane, diglyme, tetraglyme and mixtures thereof. In certain embodiments, the reduction step solvent may father comprise one or more additional hydrocarbon solvents selected from benzene, cyclohexane, methylcyclohexane, toluene, xylenes, linear and branched $C_{5-10}$alkanes, petroleum ethers, and mixtures thereof.

The isotopically enriched borate is typically added to the metal aluminum hydride/solvent mixture at a temperature and at a rate suitable to prevent uncontrolled exothermic reactions. Thus, preferred reduction steps comprise contacting the isotopically enriched borane with the metal aluminum hydride at a temperature of between about −78° C. and about 200° C. More preferably the isotopically enriched borane and the metal aluminum hydride are contacted at a temperature of between about −50° C. and about 50° C. and the mixture then heated to a temperature of between about 50° C. and about 150° C. In other preferred reduction steps provided by the instant invention, the isotopically enriched borane and the metal aluminum hydride are contacted at a temperature of between about 0° C. and about 30° C. and the mixture then heated to a reflux. In yet other preferred reduction steps of the methods of the invention, the isotopically enriched borane is added to the metal aluminum hydride mixture at a rate suitable for maintaining the mixture at a temperature below the boiling point of the mixture. In general, after all of the isotopically enriched borate is added to the metal aluminum hydride mixture, the reaction mixture is heated at reflux for between about 1 hour and about 48 hours, or more preferably for between about 1 hour and about 24 hours, or the reaction mixture is heated for between about 2 hours and about 12 hours.

The invention provides methods of synthesis of isotopically enriched metal borohydrides from isotopically enriched boric acid. Thus, the invention provides methods of preparing isotopically enriched metal borohydrides starting from isotopically enriched boric acid having 50% of the boron atoms present are $^{10}B$, at least about 80% of the boron atoms present in boric acid are $^{10}B$, at least about 90% of the boron atoms present in boric acid are $^{10}B$, at least about 95% of the boron atoms present in boric acid are $^{10}B$, or more preferably at least about 99% of the boron atoms present in boric acid are $^{10}B$. The invention further provides methods of preparing isotopically enriched metal borohydrides starting from isotopically enriched boric acid having 90% of the boron atoms present are $^{11}B$, in which at least about 95% of the boron atoms present in the boric acid are $^{11}B$, or more preferably in which at least about 99% of the boron atoms present in the boric acid $^{11}B$.

In certain other aspects, the invention provides a method of preparing isotopically enriched metal tetradecahydroundecaborate salt, the method comprising the steps of:

(a) providing isotopically enriched metal borohydride prepared according to any one of the methods described herein; and (b) contacting a solution of the isotopically enriched metal borohydride with a compound of the formula, R—X or isotopically enriched $BY_3$(ligand), under conditions conducive to the formation of a metal tetradecahydroundecaborate salt, wherein R is alkyl, alkenyl, or aralkyl;

X is fluoro, chloro, bromo, iodo, alkylsulfonate, or arylsulfonate;

Y is fluoro, chloro, or bromo; and ligand is absent, an ether, an amine, or a pyridine.

In certain other aspects, the invention provides a method of preparing isotopically enriched metal tetradecahydroundecaborate salt, the method comprising the steps of:

(a) providing isotopically enriched boric acid;

(b) contacting the isotopically enriched boric acid with an alcohol under conditions conducive to formation of an isotopically enriched borate;

(c) reducing the isotopically enriched borate with a metal aluminum hydride under conditions conducive to formation of isotopically enriched metal borohydride; and (d) contacting a solution of the isotopically enriched metal borohydride with a compound of the formula, R—X or isotopically enriched $BY_3$(ligand), under conditions conducive to the formation of a metal tetradecahydroundecaborate salt, wherein R is alkyl, alkenyl, or aralkyl;

X is fluoro, chloro, bromo, iodo, alkylsulfonate, or arylsulfonate;

Y is fluoro, chloro, or bromo; and ligand is absent, an ether, an amine, or a pyridine.

In certain preferred methods of preparing isotopically enriched metal tetradecahydroundecaborate salts, the isotopically enriched metal borohydride is contacted with a linear or branched $C_{1-10}$chloroalkane, a linear or branched $C_{1-10}$bromoalkane, a linear or branched $C_{1-10}$iodoalkane, chloro$C_{3-8}$cycloalkane, chloro$C_{5-8}$cycloalkene, bromo$C_{3-8}$cycloalkane, bromo$C_{5-8}$cycloalkene, iodo$C_{3-8}$cycloalkane, iodo$C_{5-8}$cycloalkene, $C_{6-10}$aralkylmethylchloride, $C_{6-10}$aralkylmethylbromide, $C_{6-10}$aralkylmethyliodide, or a mixture thereof. More preferably, the compound of the formula, R—X, is a compound selected from linear or branched $C_{1-10}$chloroalkane, linear or branched $C_{1-10}$bromoalkane, and a linear or branched $C_{1-10}$iodoalkane. In other preferred embodiments, the compound of the formula, R—X, is selected from linear or branched $C_{3-10}$chloroalkane, a linear or branched $C_{3-10}$bromoalkane, a linear or branched $C_{3-10}$iodoalkane. In certain particularly preferred methods of preparing isotopically enriched metal tetradecahydroundecaborate salts, the compound of the formula, R—X, is a bromoalkane or a iodoalkane such as compounds selected from the group consisting of bromobutane, iodobutane, bromopentane, iodopentane, bromohexane, iodohexane, bromoheptane, iodoheptane, bromooctane, iodooctane, benzylbromide, benzyliodide, and mixtures thereof.

In certain other preferred methods of preparing isotopically enriched metal tetradecahydroundecaborate salts, the isotopically enriched $BY_3$(ligand) is a compound in which Y is fluoro and ligand is an ether. More preferably, ligand is selected from tetrahydrofuran or diethyl ether, e.g., $BY_3$(ligand) is isotopically enriched $BF_3$-tetrahydrofuran or isotopically enriched $BF_3$—($OEt_2$).

In preferred methods of synthesis of isotopically enriched metal tetradecahydroundecaborate salts, the isotopically enriched metal borohydride is contacted with at least about one equivalent of the compound of the formula, R—X. More preferably, the metal borohydride is contacted with between about 1 and about 10 equivalents of the compound of the formula, R—X, between about 1.5 and about 7.5 equivalents of the compound of the formula, R—X, or, between about 2 and about 6 equivalents of the compound of the formula, R—X. Other preferred methods of synthesis of isotopically enriched metal tetradecahydroundecaborate salts, the isotopically enriched metal borohydride is contacted with about 2, about 2.5, about 3, about 3.5, or about 4 equivalents of the compound of the formula, R—X. In certain particularly preferred methods of synthesis of isotopically enriched metal tetradecahydroundecaborate salts, the isotopically enriched metal borohydride is contacted with about 2.5 equivalents of the compound of the formula, R—X.

In preferred methods of synthesis of isotopically enriched metal tetradecahydroundecaborate salts, the metal borohydride and the compound of the formula, R—X are contacted at a temperature of between about 50° C. and about 200° C. More preferably, the mixture of the metal borohydride and the compound of the formula, R—X, is heated to between about 60° C. and about 180° C., between about 70° C. and about 160° C., or between about 80° C. and about 140° C. Yet other preferred embodiments, the mixture is heated at a temperature of about 80° C., about 90° C., about 100° C., about 110° C., about 120° C., about 130° C., or about 140° C. In certain preferred embodiments, a condensor or other mechanism of returning volatilized material to the reaction mixture is affixed to the reactor in which the mixture of the metal borohydride and the compound of the formula, R—X, is heated to prevent volatile loss of solvent or the compound of the formula, R—X.

The mixture of the metal borohydride and the compound of the formula, R—X, is typically heated in the presence of at least one non-reactive fluid. Preferred non-reactive fluids include organic solvents having a boiling point of at least the temperature at which the mixture is heated. More particularly, the solvent may be selected from oxiranes, polyethers, aromatic hydrocarbons and the like. Certain, non-limiting, preferred solvents which are suitable for addition to the mixture of the borohydride and the compound of the formula, R—X, include dioxane, dimethoxyethane, diglyme, triglyme, tetraglyme, toluene, xylene, and mixtures thereof.

In another preferred aspect, the invention provides methods of synthesis of isotopically enriched metal tetradecahydroundecaborate salts. Thus, the invention provides methods of preparing isotopically enriched metal tetradecahydroundecaborate salts, in which at least about 50% of the boron atoms are $^{10}B$, at least about 80% of the boron atoms are $^{10}B$, at least about 90% of the boron atoms are $^{10}B$, at least about 95% of the boron atoms are $^{10}B$, or more preferably at least about 99% of the boron atoms are $^{10}B$. The invention further provides methods of preparing isotopically enriched metal tetradecahydroundecaborate salts, in which at least about 90% of the boron atoms are $^{11}B$, in which at least about 95% of the boron atoms are $^{11}B$, or more preferably in which at least about 99% of the boron atoms are $^{11}B$.

In yet other aspects, the invention provides a method of preparing isotopically enriched decaborane, the method comprising the steps of:
(a) providing isotopically enriched metal tetradecahydroundecaborate salt according to the method recited herein; and
(b) contacting the isotopically enriched metal tetradecahydroundecaborate salt with an oxidizing agent having an electrode potential of at least about 0.6 volts at a temperature of between about −10° C. and about 50° C. under conditions conducive to oxidation of the metal tetradecahydroundecaborate salt.

More particularly, the invention provides methods of preparing isotopically enriched decaborane, the method comprising the steps of:
(a) providing isotopically enriched boric acid;
(b) contacting the isotopically enriched boric acid with an alcohol under conditions conducive to formation of an isotopically enriched borate;
(c) reducing the isotopically enriched borate with a metal aluminum hydride under conditions conducive to formation of isotopically enriched metal borohydride; and
(d) contacting a solution of the isotopically enriched metal borohydride with a compound of the formula, R—X or isotopically enriched $BY_3$(ligand), under conditions conducive to the formation of a metal tetradecahydroundecaborate salt, wherein
R is alkyl, alkenyl, or aralkyl;
X is fluoro, chloro, bromo, iodo, alkylsulfonate, or arylsulfonate;
Y is fluoro, chloro, or bromo; and
ligand is absent, an ether, an amine, or a pyridine; and
(e) contacting the isotopically enriched metal tetradecahydroundecaborate salt with an oxidizing agent having an electrode potential of at least about 0.6 volts at a temperature of between about −110° C. and about 50° C. under conditions conducive to oxidation of the metal tetradecahydroundecaborate salt.

Preferred oxidation conditions suitable for use the methods of the invention include those recited in U.S. Pat. No. 4,115,521, issued to Dunks et al and *Inorganic Chemistry*, v. 20, (1981) p 1692. More preferably, oxidants suitable for the methods of synthesis provided herein include oxidants selected from $Ag^{+2}/H^+$, $Au^{+3}/H^+$, $Ce^{+4}/H$, $CeOH^{+3}/H^+$, $HClO^-/H^+$, $ClO_3^-/H^+$, $ClO_4^-/H^+$, $CO^{+3}$, $Cr^{+4}/H^+$, $Fe(phenanthroline)_3^{+3}/H^+$, $IO_3^-/H^+$, $MnO_2/H^+$, $NiO_2/H^+$, $Np^{+4}$, $O_2/H^+$, $PbO_2^-/H^+$, $PbO_2/SO_4^{2-}/H^+$, $Pu^{+4}$, $Pu^{+5}$, $RuO_4$, $Ti^{+3}$, $U^{+5}$, and $V(OH)^+$.

In another preferred aspect, the invention provides methods of synthesis of isotopically enriched decaborane. Thus, the invention provides methods of preparing isotopically enriched decaborane, in which at least about 50% of the boron atoms are $^{10}B$, at least about 80% of the boron atoms are $^{10}B$, at least about 90% of the boron atoms are $^{10}B$, at least about 95% of the boron atoms are $^{10}B$, or more preferably at least about 99% of the boron atoms are $^{10}B$. The invention further provides methods of preparing isotopically enriched decaborane, in which at least about 90% of the boron atoms are $^{11}B$, in which at least about 95% of the boron atoms are $^{11}B$, or more preferably in which at least about 99% of the boron atoms are $^{11}B$.

Certain preferred methods of synthesizing isotopically enriched decaborane is represented schematically in the flow chart, as follows:

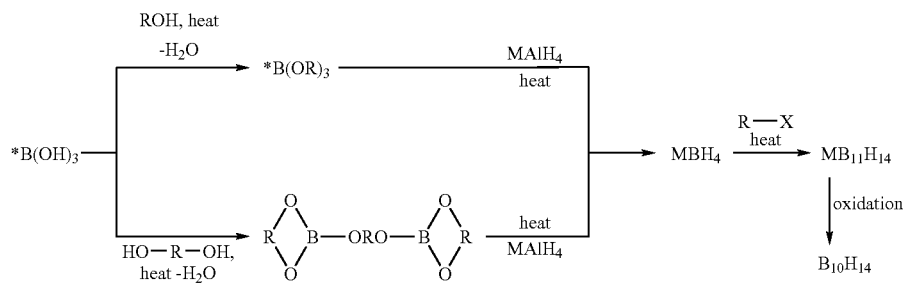

As used herein, "Borane" or "Boron hydride" refers to compounds comprising boron and hydrogen. More particularly borane or boron hydride is indented to refer to boron hydrogen compounds of the formula $B_nH_m$ where $5 \leq n \leq 100$ and $m \leq n+8$ wherein m and n satisfy the electron counting rules of macropolyhedral boranes. Although in certain embodiments additional elements may be present in the boron hydride compounds, typically neutral boron hydride compounds consist essentially of boron and hydrogen. The terms borane and boron hydride are intended to encompass isomerically pure boranes, mixtures of steroisomers, diastereomers, and structural isomers of compounds of the formula $B_nH_m$, and mixtures of boranes of the formula $B_nH_{(m)i}$ where i is the number of different boranes and (m)i is the number of hydrogen atoms in each of the i borane compounds wherein each (m)i can be the same or different. Salts comprising a boron hydride anion comprise a cation that is selected from any cationic species capable of forming a stable isolable salt. Preferred cations include monovalent and divalent cations and include, for example, alkali metals, alkaline earth metals, and ammonium cations such as trialkylammonium and tetraalkylammonium cations.

As used herein, the term "alkyl" refers to monovalent straight, branched, or cyclic alkyl groups preferably having from 1 to 20 carbon atoms, most preferably 1 to 10 carbon atoms ("lower alkyl"). This term is exemplified by groups such as methyl, ethyl, n-propyl, iso-propyl, n-butyl, iso-butyl, n-hexyl, 2-methylpropyl, 3-methylbutyl, and the like.

As used herein, the term "cycloalkane" refers to cyclic aliphatic hydrocarbons having between 3 and about 10 ring carbon atoms, or more preferably between 5 and 8 or between 5 and 7 ring carbon atoms. Cycloalkanes may be substituted with one or more alkyl group substituents. This term is exemplified by compounds such as cyclopentane, cyclohexane, methylcyclohexane and the like.

As used herein, the term "aralkyl" refers to monovalent straight, branched or cyclic alkyl groups substituted by at least one aryl group, wherein the term "aryl" indicates aromatic groups containing only carbon in the aromatic ring such as phenyl, biphenyl, 1-naphthyl and 2-naphthyl. Specifically preferred aralkyl groups include benzyl, naphthylmethyl, phenethyl, 2-phenylethyl, and the like.

As used herein, the term "halo" or "halogen" refers to fluoro, chloro, bromo, or iodo.

As to any of the above groups that contain one or more substituents, it is understood by those skilled in the art, that such groups do not contain any substitution or substitution patterns which are sterically unfeasible and or synthetically impracticable.

The following non-limiting example is illustrative of the invention. All documents mentioned herein are incorporated herein by reference.

EXAMPLE 1

$^{10}$B Tributylborate

A one-neck 500 mL round bottom flask having a Dean-Stark receiver and reflux condensor attached thereto was charged with $^{10}$B-boric acid (40 g), n-butanol (200 g), and toluene (about 100 mL). The mixture was heated to reflux and water was removed from the mixture by distillation of a toluene-water azeotrope. After removing the Dean-Stark receiver, the product mixture was fractionally distilled. $^{10}$B tributylborate was obtained as a fraction boiling at 226-228° C. under ambient pressure (195 g, 87% isolated yield).

EXAMPLE 2

$^{11}$B Enriched Tributylborate

Starting with $^{11}$B enriched boric acid, $^{11}$B tributylborate was prepared according to the procedure recited in Example 1.

EXAMPLE 3

$^{10}$B Enriched tris(2-methyl-2,4-pentanediolate)diborate

A mixture of $^{10}$B enriched boric acid, 2-methyl-2,4-pentanediol, and toluene were combined in a 1:1.5:1 molar ratio in a reactor having a Dean-Stark Receiver and a condenser attached thereto. The reaction mixture was heated to reflux and water generated by the condensation reaction was removed as a toluene-water azeotrope. The mixture was heated until the three molar equivalents of water had been collected in the Dean-Stark trap. The reaction mixture comprises the product $^{10}$B Enriched tris(2-methyl-2,4-pentanediolate)diborate in essentially quantitative yield and toluene. The mixture may be contacted directly with metal aluminum hydride in the next step of the metal borohydride synthesis. Alternatively, the $^{10}$B Enriched tris(2-methyl-2,4-pentanediolate)diborate may be purified by toluene removal under a reduced pressure atmosphere.

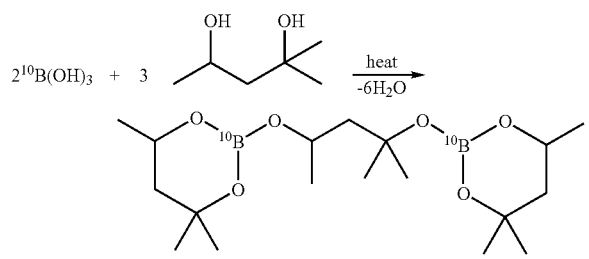

EXAMPLE 4

$^{11}$B Enriched tris(2-methyl-2,4-pentanediolate)diborate was prepared by the method of Example 3 wherein $^{11}$B enriched boric acid was used in place of $^{10}$B boric acid.

EXAMPLE 5

$^{11}$B Enriched Sodium Borohydride

A five liter 3-neck flask equipped with an overhead stirrer and a reflux condenser was charged with anhydrous tetrahydrofuran (1 L) and anhydrous diethyl ether (700 mL) under an argon atmosphere. Sodium aluminum hydride (105 g, ca 86% purity, 1.77 mole) was added to the reaction flask and a pressure equalized addition funnel was charged with $^{11}$B enriched tributylborate (427 mL, 1.57 mole) which was prepared in Example 2. The borate was added dropwise to a stirred reaction mixture and the reaction mixture was gradually heated to reflux and maintained at reflux for several hours. Upon cooling, crude solid $^{11}$B enriched sodium borohydride was filtered under a positive pressure of argon atmosphere, the solid was washed with dry toluene to remove aluminum butoxide byproducts, and the toluene removed by filtration under a positive pressure argon atmosphere. The toluene wash and filtration process is repeated as necessary to remove residual aluminum butoxide byproducts. Yield: 55.5 g, 1.46 mole, 93.1%. The only boron species observed by $^{11}$B NMR spectroscopy is the resonance corresponding to $^{11}$BH$_4$ (a 1:4:6:4:1 quintet centered at −37 ppm). If necessary, $^{11}$B enriched Na$^{11}$BH$_4$ can be further purified by recrystallization from diglyme or by extraction with liquid ammonia. The resulting products retain the isotopic purity of the starting $^{11}$B enriched $^{11}$B(OH)$_3$, and $^{11}$B enriched tributylborate. This preparation has been successfully scaled up to multi-kilogram quantities without loss of product quality.

EXAMPLE 6

$^{10}$B Enriched Lithium Borohydride

A round bottom flask was charged with lithium aluminum hydride (5.5 g) in anhydrous tetrahydrofuran (40 mL), anhydrous diethyl ether (70 mL), and a magnetic stirbar under an argon atmosphere. A toluene solution containing the tris(2-methyl-2,4-pentanediolate)diborate prepared in Example 3 was added dropwise to the reaction mixture from a pressure equalized dropping funnel. The reaction mixture was then heated for 15 hrs. After cooling, the precipitate was filtered to remove aluminum alkoxide byproducts. The clear filtrate contains $^{10}$B enriched lithium borohydride as the only boron species (evidenced the $^{10}$B NMR spectra which contains a sole resonance at −37 ppm (a 1:4:6:4:1 quintet). No other boron resonance was observed. Lithium borohydride was precipitated from solution by addition of 1,4-dioxane, which can be subsequently removed by heating the isolated solid in vacuo to yield $^{10}$B enriched litium borohydride.

EXAMPLE 7

Preparation of Na$^{11}$B$_{11}$H$_{14}$ and $^{11}$B$_{10}$H$_{14}$

Na$^{11}$BH$_4$ is readily converted into B-11 enriched decaborane, $^{11}$B$_{10}$H$_{14}$, via Na$^{11}$B$_{11}$H$_{14}$ by the methods described in U.S. Pat. Nos. 4,153,672; 4,115,520; and 4,115,521, issued to Dunks, et al., and academic publications, Dunks, et al., *Inorganic Chemistry*, v. 17, (1978) p 1514 and Dunks, et al., *Inorganic Chemistry*, v. 20, (1981) p 1692. The resulting products retain the isotopic purity of the starting $^{11}$B enriched Na$^{11}$BH$_4$.

The following procedure was used to prepare the $^{11}$B enriched tetradecahydroundecaborate(1-) ion, [$^{11}$B$_{11}$H$_{14}$]$^-$, from $^{11}$B enriched sodium borohydride. A 6 liter four necked round bottom flask (placed in a heating mantle) was equipped with a thermometer adapter with thermometer inserted and connected to an argon source. An overhead stirrer was inserted in the center neck. A pressure equalized addition funnel was inserted into a third neck. Lastly, a cold water condenser was inserted into the fourth neck with the exit of the condenser leading to an acetone filled scrubber. With the apparatus thoroughly dried and purged with argon, the flask was sequentially charged with $^{11}$B enriched sodium borohydride (58 g, 1.54 mole) and dry diglyme (600 mL). The reaction mixture was then heated to 105° C. and n-bromopentane (480 mL, 3.85 mole) was added dropwise from the addition funnel over a period of five hours while maintaining the reaction mixture temperature at 105±5° C. The mixture was further heated until evolution of gases practically ceased.

After the reaction mixture was cooled to room temperature, the resulting slurry was filtered and washed with diethyl ether. Volatile compounds of the combined filtrate were removed under vacuum. The resulting oil is dissolved in water, triethylammonium chloride was added to induce precipitation of (HNEt$_3$)[$^{11}$B$_{11}$H$_{14}$]. An isolated yield of 60-67% is typical.

For conversion to B-11 enriched decaborane, the triethylammoniun salt is first converted to the potassium or sodium salt for solubility in water. Conversion to decaborane can be accomplished by oxidizing the [$^{11}$B$_{11}$H$_{14}$] salt as described in U.S. Pat. No. 4,115,521, issued to Dunks et al and *Inorganic Chemistry*, v. 20, (1981) p 1692. Alternatively, the sodium salt of $^{11}$B enriched B$_{11}$H$_{14}$$^-$ can be carried through directly to $^{11}$B enriched decaborane following removal of diglyme solvent as described in U.S. Pat. No. 4,115,521, issued to Dunks et. al. and *Inorganic Chemistry*, v. 20, (1981) p 1692.

The invention has been described in detail with reference to preferred embodiments thereof. However, it will be appreciated that those skilled in the art, upon consideration of the disclosure, may make modifications and improvements within the spirit and scope of the invention.

What is claimed is:

1. A method of synthesizing an isotopically enriched metal borohydride, the method comprising the steps of:
   (a) providing isotopically enriched boric acid;
   (b) contacting the isotopically enriched boric acid with an alcohol under conditions conducive to formation of an isotopically enriched borate; and (c) reducing the isotopically enriched borate with a metal aluminum hydride under conditions conducive to formation of isotopically enriched metal borohydride.

2. The method of claim 1, wherein the isotopically enriched borate is a compound of Formula I:

[(RO)$_2$B—O—]$_n$—R' wherein each occurrence of R is independently selected from the group consisting of linear or branched alkyl, cycloalkyl, cycloalkyl-alkyl, alkenyl, aryl, aralkyl, haloalkyl, and alkylether, or two R groups taken in combination form α,ω-alkylene group or a 1,2-cylcoalkylene group each of which may be optionally substituted with one or more groups selected from the group consisting of alkyl, alkenyl, cycloalkyl, cycloalkyl-alkyl, aryl, aralkyl, and alkoxy;

n is 1 or 2; and

R' is selected from the group consisting of alkyl, alkenyl, aryl, aralkyl, haloalkyl, and alkylether when n=1, or R' is a α,ω-alkylene group or a 1,2-cylcoalkylene group each of which may be optionally substituted with one or more groups selected from the group consisting of alkyl, alkenyl, cycloalkyl, cycloalkyl-alkyl, aryl, aralkyl, and alkoxy when n=2.

3. The method of claim 1, wherein the isotopically enriched borate is a compound of the formula, B(OR)$_3$, wherein R is independently selected at each occurrence from the group consisting of linear or branched C$_{1-10}$alkyl, phenyl, benzyl, C$_{3-8}$cycloalkyl, C$_{3-8}$cycloalkyl-C$_{1-10}$alkyl, C$_{2-10}$alkenyl, C$_{1-10}$alkoxy, C$_{1-10}$haloalkyl, and C$_{2-10}$alkylether.

4. The method of claim 3, wherein the isotopically enriched borate is a compound of the formula, B(OR)$_3$, wherein each occurrence of R is the same and R is selected from the group consisting of linear or branched C$_{1-10}$alkyl, phenyl, benzyl, C$_{3-8}$cycloalkyl, C$_{3-8}$cycloalkyl-C$_{1-10}$alkyl, C$_{2-10}$alkenyl, C$_{1-10}$alkoxy, C$_{1-10}$haloalkyl, and C$_{2-10}$alkylether.

5. The method of claim 1, wherein the isotopically enriched borate is a compound of Formula II:

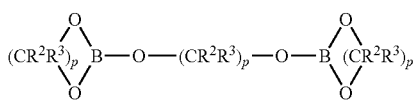

wherein R$^2$ and R$^3$ are independently selected at each occurrence from the group consisting of hydrogen, linear or branched alkyl, cycloalkyl, cycloalkyl-alkyl, alkenyl, aryl, aralkyl, haloalkyl, and alkylether; and p is an integer selected from 1-5.

6. The method of claim 5, wherein the isotopically enriched borate is a compound of the formula:

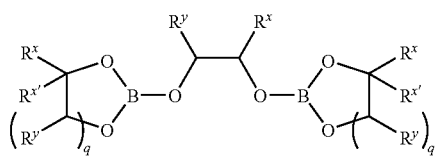

wherein q is 1 or 2; and

R$^x$, R$^{x'}$, and R$^y$ are independently selected at each occurrence from the group consisting of hydrogen, linear and branched C$_{1-10}$alkyl, C$_{1-10}$alkoxy, and C$_{3-8}$cycloalkyl, or R$^x$ and R$^y$, taken in combination form a α,ω-alkylene group.

7. The method of claim 6, wherein R$^x$ and R$^y$ are selected from the group consisting of hydrogen and linear or branched C$_{1-4}$alkyl.

8. The method of claim 1, wherein esterification step comprises contacting isotopically enriched boric acid with at least three equivalents of a linear or branched C$_{1-10}$alkanol or at least one and a half (1.5) equivalents of a C$_{2-10}$alkanediol.

9. The method of claim 8, wherein the esterification step comprises contacting the isotopically enriched boric acid with at least three equivalents of a linear C$_{2-10}$alkanol or at least one and a half (1.5) equivalents of a linear or branched 1,2-C$_{2-10}$alkanediol.

10. The method of claim 9, wherein the esterification step comprises contacting the isotopically enriched boric acid with about three equivalents of a linear C$_{2-10}$alkanol or about one and a half (1.5) equivalents of a linear or branched 1,2-C$_{2-10}$alkanediol.

11. The method of claim 1, wherein water generated during the esterification step is removed from the reaction mixture.

12. The method of claim 1, wherein the water is removed from the reaction mixture by distillation.

13. The method of claim 12, wherein the water is removed as an azeotrope with a member selected from the group consisting of toluene, xylene, benzene, 1,2-dichloroethane, and mixtures thereof.

14. The method of claim 1, wherein the esterification step is conducted at a temperature of above about 80° C.

15. The method of claim 1, wherein the esterification step is conducted at a temperature of between about 95° C. and about 175° C.

16. The method of claim 1, wherein the reduction step comprises contacting the borate with a mixture of a metal aluminum hydride and at least one solvent.

17. The method of claim 16, wherein at least one solvent is selected from the group consisting of diethyl ether, tetrahydrofuran, 1,3-dioxolane, 1,4-dioxane, 1,3-dioxane, methyl-tert-butyl ether, dimethoxyethane, diglyme, and mixtures thereof.

18. The method of claim 17, wherein the mixture comprises at least one additional hydrocarbon solvent selected from the group consisting of benzene, cyclohexane, methylcyclohexane, toluene, xylenes, linear and branched C$_{5-10}$alkanes, petroleum ethers, and mixtures thereof.

19. The method of claim 1, wherein the metal aluminum hydride is selected from the group consisting of Group I and Group II metal Aluminum hydrides, and mixtures thereof.

20. The method of claim 19, wherein the metal aluminum hydride is lithium aluminum hydride or sodium aluminum hydride.

21. A method of preparing isotopically enriched metal tetradecahydroundecaborate salt, the method comprising the steps of:

(a) providing isotopically enriched metal borohydride by carrying out the method of claim 1; and (b) contacting a solution of the isotopically enriched metal borohydride with a compound of the formula, R—X or isotopically enriched $BY_3$(ligand), under conditions conducive to the formation of a metal tetradecahydroundecaborate salt, wherein R is alkyl, alkenyl, or aralkyl;

X is fluoro, chloro, bromo, iodo, alkylsulfonate, or arylsulfonate;

Y is fluoro, chloro, or bromo; and the ligand of $BY_3$(ligand) is absent, an ether, an amine, or a pyridine.

22. The method of claim 21, wherein the metal borohydride and the compound of the formula, R—X are contacted at a temperature of between about 50° C. and about 200° C. or wherein the metal borohydride and the isotopically enriched compound of the formula, $BY_3$(ligand) are contacted at a temperature of between about 50° C. and about 200° C.

* * * * *